United States Patent

Kennedy et al.

Patent Number: 5,314,989
Date of Patent: * May 24, 1994

[54] ABSORBABLE COMPOSITION

[75] Inventors: John Kennedy, Stratford; Donald S. Kaplan, Weston; Ross R. Muth, Brookfield, all of Conn.

[73] Assignee: United States Surgical Corporation, Norwalk, Conn.

[*] Notice: The portion of the term of this patent subsequent to Jul. 6, 2010 has been disclaimed.

[21] Appl. No.: 58,515

[22] Filed: May 3, 1993

Related U.S. Application Data

[63] Continuation-in-part of Ser. No. 686,815, Apr. 17, 1991, Pat. No. 5,225,520.

[51] Int. Cl.$^5$ .............................................. C08G 63/08
[52] U.S. Cl. ................................... 528/354; 525/408; 525/415; 606/230; 606/231
[58] Field of Search .................. 128/335.5; 523/105; 525/408, 415; 528/354, 357; 606/230, 231

[56] References Cited

U.S. PATENT DOCUMENTS

| | | | |
|---|---|---|---|
| 3,839,297 | 10/1974 | Wasserman et al. | 528/354 |
| 4,052,988 | 10/1977 | Doddi et al. | 128/335.5 |
| 4,243,775 | 1/1981 | Rosensaft et al. | 525/415 |
| 4,300,565 | 11/1981 | Rosensaft et al. | 128/335.5 |
| 4,429,080 | 1/1984 | Casey et al. | 525/415 |
| 4,438,253 | 3/1984 | Casey et al. | 528/86 |
| 4,440,789 | 4/1984 | Mattei et al. | 428/78 |
| 4,452,973 | 6/1984 | Casey et al. | 528/354 |
| 4,595,713 | 6/1986 | St. John | 523/105 |
| 4,643,191 | 2/1987 | Bezwada et al. | 128/335.5 |
| 4,646,741 | 3/1987 | Smith | 128/334 |
| 4,653,497 | 3/1987 | Bezwada et al. | 128/335.5 |
| 4,716,203 | 12/1987 | Casey et al. | 525/408 |
| 4,744,365 | 5/1988 | Kaplan et al. | 128/335.5 |
| 4,788,979 | 6/1988 | Jarrett et al. | 128/335.5 |
| 4,838,267 | 6/1989 | Jamiolkowski et al. | 128/335.5 |
| 4,857,602 | 8/1989 | Casey et al. | 525/408 |
| 5,007,923 | 4/1991 | Bezwada et al. | 606/231 |
| 5,019,094 | 5/1991 | Bezwada et al. | 606/230 |
| 5,047,048 | 9/1991 | Bezwada et al. | 606/231 |
| 5,080,665 | 1/1992 | Jarrett et al. | 606/219 |
| 5,123,912 | 6/1992 | Kaplan et al. | 606/230 |
| 5,252,701 | 10/1993 | Jarrett et al. | 528/354 |

FOREIGN PATENT DOCUMENTS 0411545 2/1991 European Pat. Off. .
0440448 8/1991 European Pat. Off. .

Primary Examiner—Nathan M. Nutter
Assistant Examiner—Shelley A. Dodson

[57] ABSTRACT

A block copolymer for use in the fabrication of bioabsorbable articles such as monofilament surgical sutures is prepared by copolymerizing one or more hard phase forming monomers and 1,4-dioxan-2-one, and then polymerizing one or more hard phase forming monomers with the dioxanone-containing copolymer.

30 Claims, No Drawings

ABSORBABLE COMPOSITION

This application is a continuation-in-part of copending application Ser. No. 07/686,815 filed Apr. 17, 1991 now U.S. Pat. No. 5,225,520.

BACKGROUND OF THE INVENTION

1. Field of the Invention

This invention relates to a copolymer, and more particularly to a surgical article manufactured from the copolymer and to a method of manufacturing the copolymer and surgical article.

2. Background of the Art

Absorbable synthetic polymer sutures known in the prior art are usually manufactured, sold, and used as multifilament braids. The known absorbable polymers containing a glycolic acid ester linkage seem to be well suited for use in fabricating braided sutures. However, monofilament sutures fabricated from such polymers tend to be relatively stiff, particularly in the larger diameters. Yet, some surgeons prefer the suturing characteristics of a monofilament suture because of its smooth, continuous-surface. Thus, it has been recognized for some years that there is a need in surgery for flexible, absorbable, monofilament sutures which retain a safe and useful proportion of their strength for a relatively long period of time in vivo.

To be fully useful as an absorbable suture it is essential that a monofilament or multifilament not only be absorbable and flexible but it must also be capable of a relatively long period of in vivo strength retention. An appropriate strength retention target for this type suture is considered to be about 35-70 days in vivo.

U.S. Pat. No. 4,429,080 to Casey et al discloses a triblock copolymer wherein the end blocks comprise polyglycolide, and the middle block comprises a glycolide/trimethylene carbonate copolymer.

A new polymer has been developed for use in the fabrication of absorbable monofilament or multifilament sutures.

SUMMARY OF THE INVENTION

Provided herein is a block copolymer for use in the fabrication of bioabsorbable articles and a method for making the same. The block copolymer is composed of a first block made from one or more hard phase forming monomers and a second block made from 1,4-dioxane-2-one randomly combined with at least one monomer selected from the group consisting of hard phase forming monomers.

In particularly useful embodiments, the block copolymer is composed of glycolide as one block, and random lactide/dioxanone copolymer as the other block. The lactide and dioxanone are first copolymerized at a first reaction temperature. The reaction temperature is then increased and glycolide is added to the reaction mixture. The resulting copolymer can be fabricated into both monofilament and multifilament absorbable sutures with advantageous flexibility and knot pull characteristics.

DETAILED DESCRIPTION OF PREFERRED EMBODIMENTS

Bioabsorbable materials useful for fabricating surgical articles, such as sutures, surgical clips, etc., include homopolymers and copolymers of glycolide, lactide, 1,4-dioxanone, trimethylene carbonate, and caprolactone.

The present invention relates to a block copolymer having one block composed of units of hard phase forming monomers. The term "hard phase forming monomers" as used herein includes lactide (including for example, l-lactide, d-lactide, meso-lactide and dl-lactide having variable ratios of d to l), glycolide, mixtures of glycolide and lactide, and other monomers or mixtures of monomers that form absorbable polymers with glass transition temperatures above room temperature. In particularly useful embodiments, the block of hard phase forming monomers is composed of units of glycolide:

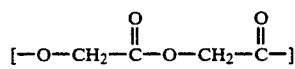

Another block of the copolymers of this invention is composed of a random copolymer of 1,4-dioxan-2-one and at least one hard phase forming monomer. In particularly useful embodiments, the other block is composed of units of L-lactide:

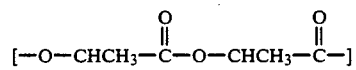

copolymerized with randomly intermingled units of 1,4-dioxan-2-one:

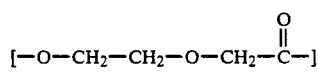

The block copolymer is preferably a diblock copolymer prepared by first copolymerizing the hard phase forming monomer with 1,4-dioxan-2-one and then polymerizing that copolymer with the hard phase forming monomer(s) of the other block.

Catalysts suitable for carrying out the polymerization include compounds of tin, aluminum, antimony, lead, boron, and titanium. A preferred catalyst is stannous octoate. Other catalysts include stannous chloride, dibutyl tin dilaurate, dibutyl tin diacetate, dibutyl tin dichloride, stannic chloride pentahydrate, aluminum isopropoxide, antimony trioxide, stannic fluoride, stannous citrate, stannous acetate, antimony trifluoride, tin tetraisopropoxide, lead oxide, tetraisopropyl titanate, titanium acetyl acetonate, tetraoctylene glycol titanate, boron trifluoride etherate, and aluminum trichloride.

The block made entirely of hard phase forming monomer(s) can constitute from about 10 to about 90 weight percent of the block copolymer, and preferably constitutes from about 50 to about 85 weight percent of the block copolymers. In the block made from 1,4-dioxan-2-one, the hard phase forming monomer(s) can constitute from about 1 to about 50 weight percent of the block and preferably constitutes from about 5 to about 35 weight percent of the block.

The preferred composition range of the monomer units of particularly useful block copolymers in terms of weight % of the final block copolymer is set forth below in Table 1.

TABLE 1

| Monomer unit | Block Copolymer Composition (weight percent) | |
|---|---|---|
| | Broad Range | Preferred Range |
| glycolide | 55% to 85% | 65% to 75% |
| lactide | 1% to 20% | 3% to 8% |
| 1,4-dioxanone | 10% to 40% | 20% to 30% |

In the examples below a preferred composition of the block copolymer of the present invention includes 70 wt % of glycolide, 25.5 wt. % 1,4-dioxan-2-one, and 4.5 wt. % lactide.

The polymerization reaction may be carried out at a temperature of from 100° C. to 250° C. The first step is the polymerization of the lactide and 1,4-dioxan-2-one, which is carried out at a temperature of between about 100° C. and 150° C. and preferably about 120° C. This reaction temperature is maintained until the polymerization is substantially completed, i.e., about 30 minutes.

The second step comprises raising the reaction temperature to between about 200° C. and 250° C., and adding glycolide preferably when the temperature has reached about 200° C. The glycolide will then copolymerize with the lactide/dioxanone copolymer to create a separate block in a diblock copolymer.

The resulting copolymer may then be subjected to further processing such as extruding, drawing, relaxing, etc.

The preferred area for use of the present invention is in the fabrication of sterile synthetic absorbable surgical articles, specifically sutures, wherein glycolide is employed as the predominant monomer. The sutures may be either multifilament or monofilament. Absorbable monofilament sutures fabricated from such copolymers have been found to be useful in that they are more flexible and more resistant to in vivo strength loss than corresponding size monofilament sutures fabricated from a polymer containing only glycolic acid ester linkage.

The surgical articles are fabricated from the copolymer using conventionally employed forming procedures, such as extrusion, and subsequently sterilized. The resulting surgical articles are employed in a conventional manner.

Surgical sutures fabricated from the polymer of the present invention display good flexibility and knot pull strength.

The following examples illustrate procedures which are useful in conjunction with the practice of the present invention but are not to be taken as being limiting thereto.

EXAMPLE 1

A conventional polymerization reactor was preheated to a temperature of 120° C. Quantities of 510 grams of 1,4-dioxanone, and 90 grams of L-lactide were added to the reactor with 0.2 grams of stannous octoate catalyst. The reactor was held at 120° C. for 60 hours until copolymerization was substantially completed. A sample of the polymer, designated as Sample 1, was taken at this point. Then the reactor temperature was gradually increased. When the reactor temperature reached 180° C., Sample 2 was taken of the polymer. When the temperature reached 200° C., 1400 grams of glycolide was added to create a block copolymer having at least one glycolide block and at least one lactide/dioxanone block. When the reactor temperature reached 220° C. the polymer was stirred for 10 minutes. The polymer was then extruded and Sample 3 was taken. Samples 1, 2, and 3 were tested for inherent viscosity (dl/g), and enthalpy change ($\Delta H$) in calories/gram.

The enthalpy was measured on a differential scanning calorimeter which measured the specific heat of the sample over a range of temperatures with a scan rate of 20° C./min. The change in enthalpy is an indication of the extent of crystallinity.

The inherent viscosity of a polymer is an indicator of its molecular weight, and was measured for the above-mentioned samples in accordance with standard measuring techniques and equipment known to those skilled in the art.

Table 2 below sets forth inherent viscosity and enthalpy data for samples 1, 2, and 3.

TABLE 2

| Sample | Inherent Viscosity | Enthalpy ($\Delta H$) at $T_{max}$ |
|---|---|---|
| 1 | 0.61 | 11.1 @ 59° C. |
| 2 | 0.61 | 10.63 @ 59° C. |
| 3 | 0.90 | 14.99 @ 211° C. |

The above data indicate that sample 3, which was taken from the polymer after the glycolide was copolymerized with the lactide/dioxanone copolymer, exhibited a higher inherent viscosity and, therefore, a higher molecular weight. This indicates copolymerization of the glycolide occurred. Also shown is a greater $\Delta H$, which indicates a greater degree of crystallinity. These physical properties, i.e., higher molecular weight and greater crystallinity, indicate that the material is suitable for fabrication into a fiber.

EXAMPLE 2

The block copolymer of Example 1 was extruded, ground and dried at from 20° to 120° C. at a pressure of less than 10 torr. The resulting material was then formed by extrusion into a monofilament with an Instron rheometer (Dc=0.0301"; Lc=1.001") at a temperature of 203° C. The extrusion speed was 3 inches per minute. The monofilament was then dried at room temperature overnight. The monofilament was then drawn at a 4.5× draw ratio in an oven at 60° C. by being passed around two godgets. The first godget providing a linear tangential velocity of 10 feet per minute and the second godget providing a linear tangential velocity of 45 feet per minute.

The drawn monofilament was then tested for straight pull and knot pull strength. An Instron Series 1X Automated Materials Testing System v4.03e was employed with the following parameters and conditions: Interface type 1011 series; Sample rate=20.00 pts/sec.; crosshead speed=2.0 inches/min.; humidity=50%; temperature=73° F. Specimens of the monofilament were tested and the results of the testing are set forth below in Table 3.

TABLE 3

| (Specimen diameter = 0.0073 inches/0.1854 mm) | | |
|---|---|---|
| | STRAIGHT PULL | KNOT-PULL |
| Avg. load @ maximum load (lbs.) | 3.111 | 2.780 |
| Avg. Elongation at maximum load % | 27.59 | 22.470 |
| Avg. Young's Modulus | 541.8 | — |

TABLE 3-continued (Specimen diameter = 0.0073 inches/0.1854 mm)

| | STRAIGHT PULL | KNOT-PULL |
|---|---|---|
| (kpsi) | | |

EXAMPLE 3

The filament of Example 2 was then subjected to controlled shrinkage or relaxation in accordance with the following method.

The monofilament was placed in a hot air oven at a temperature of 75° C. for 10 minutes. The length of the filament before treatment was 91.8 cm. After treatment, the filament length was 82.6 cm. Thus, the observed shrinkage was 10%.

After relaxation, the filament was tested for inherent viscosity and mechanical properties in accordance with the methods as described in Examples 1 and 2. The results of the testing are set forth below in Table 4.

TABLE 4

| Post shrinkage data | |
|---|---|
| Inherent viscosity | 0.79/0.82 |
| Diameter | 0.209 mm (.00823 inches) |
| Avg. load at maximum load (knot pull) | 1.24 kg (2.728 lbs.) |
| Avg. load at maximum load (straight pull) | 1.45 kg (3.20 lbs.) |
| Elongation at maximum load (straight pull) | 39% |
| Young's Modulus (straight pull) | 513.2 kpsi |

The data of the above examples indicate that the copolymer of the present invention is advantageous for the manufacture of a monofilament suture. The block copolymer described above is bioabsorbable and, as seen from the Young's modulus value, is flexible, strong, and possesses advantageous handling characteristics.

What is claimed is:

1. A block copolymer which comprises a proportion of units of one or more hard phase forming monomers as one of said blocks, and another of said blocks comprising a proportion of units having the formula:

$$[-O-CH_2-CH_2-O-CH_2-\overset{O}{\underset{\|}{C}}-]$$

randomly combined with a proportion of units of one or more hard phase forming monomers.

2. The block copolymer of claim 1 wherein said block copolymer is a diblock copolymer.

3. The block copolymer of claim 1 wherein said one or more hard phase forming monomers are selected from the group consisting of glycolide, lactide and mixtures thereof.

4. The block copolymer of claim 1 wherein from about 1 weight % to about 20 weight % of the block copolymer comprises units having the formula:

$$[-O-CHCH_3-\overset{O}{\underset{\|}{C}}-O-CHCH_3-\overset{O}{\underset{\|}{C}}-].$$

5. The block copolymer of claim 1 wherein the hard phase forming monomers comprise about 10 weight % to about 40 weight % of the block containing units of formula:

$$[-O-CH_2-CH_2-O-CH_2-\overset{O}{\underset{\|}{C}}-].$$

6. A surgical article manufactured from a block copolymer which comprises a proportion of units of one or more hard phase forming monomers as one of said blocks, and another of said blocks comprising a proportion of units having the formula:

$$[-O-CH_2-CH_2-O-CH_2-\overset{O}{\underset{\|}{C}}-]$$

randomly combined with a proportion of units of one or more hard phase forming monomers.

7. The surgical article of claim 6 wherein said block copolymer is a diblock copolymer.

8. The surgical article of claim 6 wherein said surgical article is a suture.

9. The surgical article of claim 8 wherein said suture is a monofilament suture.

10. The surgical article of claim 6 wherein from about 1 weight % to about 20 weight % of the block copolymer comprises units having the formula:

$$[-O-CHCH_3-\overset{O}{\underset{\|}{C}}-O-CHCH_3-\overset{O}{\underset{\|}{C}}-].$$

11. A method for preparing a bioabsorbable block copolymer, comprising:

a) polymerizing a mixture of one or more hard phase forming monomers and 1,4-dioxan-2-one at a first reaction temperature to create a copolymer thereof;

b) polymerizing one or more hard phase forming monomers with the copolymer of step (a) at a second reaction temperature to create the bioabsorbable block copolymer.

12. The method of claim 11 wherein said block copolymer is a diblock copolymer.

13. The method of claim 11 wherein said first reaction temperature comprises a temperature of from about 100° C. to about 150° C.

14. The method of claim 11 wherein said second reaction temperature comprises a temperature of from about 200° C. to about 250° C.

15. The method of claim 11 wherein step (a) is carried out in the presence of a polymerization catalyst.

16. The method of claim 15 wherein said catalyst is stannous octoate.

17. The method of claim 15 wherein said catalyst is selected from the group consisting of stannous chloride, dibutyl tin dilaurate, dibutyl tin diacetate, dibutyl tin dichloride, stannic chloride pentahydrate, aluminum isopropoxide, antimony trioxide, stannic fluoride, stannous citrate, stannous acetate, antimony trifluoride, tin tetraisopropoxide, lead oxide, tetraisopropyl titanate, titanium acetyl acetonate, tetraoctylene glycol titanate, boron trifluoride etherate, and aluminum trichloride.

18. A method for making a bioabsorbable surgical article, comprising:

a) polymerizing a mixture of one or more hard phase forming monomers and 1,4-dioxan-2-one at a first reaction temperature to create a copolymer thereof;

b) polymerizing one or more hard phase forming monomers with the copolymer of step (a) at a second reaction temperature to create a bioabsorbable block copolymer;

c) forming a surgical article from said block copolymer.

19. The method of claim 18 wherein said forming includes the step of extruding the block copolymer into a filament.

20. The method of claim 19 wherein the bioabsorbable surgical article comprises a suture.

21. The method of claim 20 additionally comprising drawing the suture and relaxing the suture.

22. The method of claim 18 wherein said block copolymer is a diblock copolymer.

23. The method of claim 18 wherein said first reaction temperature comprises a temperature of from about 100° C. to about 150° C.

24. The method of claim 18 wherein said second reaction temperature comprises a temperature of from about 200° C. to about 250° C.

25. The method of claim 18 wherein step (a) is carried out in the presence of a polymerization catalyst.

26. The method of claim 25 wherein said catalyst is stannous octoate.

27. The method of claim 25 wherein said catalyst is selected from the group consisting of stannous chloride, dibutyl tin dilaurate, dibutyl tin diacetate, dibutyl tin dichloride, stannic chloride pentahydrate, aluminum isopropoxide, antimony trioxide, stannic fluoride, stannous citrate, stannous acetate, antimony trifluoride, tin tetraisopropoxide, lead oxide, tetraisopropyl titanate, titanium acetyl acetonate, tetraoctylene glycol titanate, boron trifluoride etherate, and aluminum trichloride.

28. The method of claim 18 wherein from about 55 weight % to about 85 weight % of the block copolymer comprises units derived from glycolide.

29. The method of claim 18 wherein from about 1 weight % to about 20 weight % of the block copolymer comprises units derived from lactide.

30. The method of claim 18 wherein from about 10 weight % to about 40 weight % of the block copolymer comprises units derived from 1,4-dioxan-2-one.

* * * * *